United States Patent
Axelsson et al.

(10) Patent No.: US 9,597,017 B2
(45) Date of Patent: Mar. 21, 2017

(54) METHOD AND APPARATUS FOR DETECTING LAMENESS IN LIVESTOCK

(71) Applicant: DELAVAL HOLDING AB, Tumba (SE)

(72) Inventors: Thomas Axelsson, Farsta (SE); Gunnar Brostedt, Marsta (SE)

(73) Assignee: DeLaval Holding AB, Tumba (SE)

( * ) Notice: Subject to any disclaimer, the term of this patent is extended or adjusted under 35 U.S.C. 154(b) by 411 days.

(21) Appl. No.: 14/345,408

(22) PCT Filed: Oct. 5, 2012

(86) PCT No.: PCT/SE2012/051063
§ 371 (c)(1),
(2) Date: Mar. 18, 2014

(87) PCT Pub. No.: WO2013/052001
PCT Pub. Date: Apr. 11, 2013

(65) Prior Publication Data
US 2014/0350410 A1    Nov. 27, 2014

Related U.S. Application Data

(60) Provisional application No. 61/543,867, filed on Oct. 6, 2011.

(30) Foreign Application Priority Data

Oct. 6, 2011   (SE) ...................................... 1150925

(51) Int. Cl.
  *A61B 5/00*   (2006.01)
  *A61B 5/11*   (2006.01)
(Continued)

(52) U.S. Cl.
  CPC .......... *A61B 5/1128* (2013.01); *A01K 29/005* (2013.01); *A61B 5/0077* (2013.01);
(Continued)

(58) Field of Classification Search
None
See application file for complete search history.

(56) References Cited

U.S. PATENT DOCUMENTS 6,699,207 B2   3/2004  Tasch et al.
7,335,168 B2 *  2/2008  Rugg .................... A61B 5/1113
                                                  119/712
(Continued)

FOREIGN PATENT DOCUMENTS

RU   2010106264 A    9/2011
WO   2006/009959 A2  1/2006
WO   2011/051693 A1  5/2011

OTHER PUBLICATIONS

Supplementary International Search Report, dated Dec. 4, 2013, from corresponding PCT application.
(Continued)

*Primary Examiner* — Long V Le
*Assistant Examiner* — Bradley Impink
(74) *Attorney, Agent, or Firm* — Young & Thompson

(57) ABSTRACT

A device and method for detecting lameness in a standing animal uses at least one optical imaging device coupled to processing arrangement. The optical imaging device is arranged in a position to capture at least one image showing the lower portions of at least one leg of an animal and to forward the image to the processing arrangement, which, in turn, analyses the image to determine a condition of lameness when said at least one leg is held in a raised position on or above ground level. The system is particularly suited to detecting lameness in dairy animals and can be integrated in
(Continued)

a milking or feeding stall or with an automatic or semi-automatic milking system.

19 Claims, 2 Drawing Sheets

(51) Int. Cl.
  *A01K 29/00* (2006.01)
  *A01K 1/12* (2006.01)
(52) U.S. Cl.
  CPC ............... *A61B 5/112* (2013.01); *A01K 1/12* (2013.01); *A61B 2503/40* (2013.01)

(56) References Cited

U.S. PATENT DOCUMENTS

| | | | |
|---|---|---|---|
| 8,488,844 B2 | 7/2013 | Springer et al. | |
| 2002/0037092 A1 | 3/2002 | Craig et al. | |
| 2004/0023612 A1 | 2/2004 | Kriesel | |
| 2004/0199089 A1 | 10/2004 | Tasch et al. | |
| 2005/0257748 A1 | 11/2005 | Kriesel et al. | |
| 2006/0000420 A1* | 1/2006 | Davies | A01K 11/008 119/174 |
| 2006/0155172 A1 | 7/2006 | Rugg | |
| 2010/0006034 A1* | 1/2010 | Van Den Berg | A01K 5/02 119/14.18 |
| 2010/0107985 A1* | 5/2010 | O'Hare | A01K 29/005 119/174 |
| 2010/0179454 A1 | 7/2010 | Davies | |
| 2010/0246970 A1* | 9/2010 | Springer | A01K 11/006 382/195 |
| 2010/0269582 A1 | 10/2010 | Bareket et al. | |
| 2012/0274442 A1* | 11/2012 | Mottram | A61B 5/1038 340/5.8 |
| 2013/0319336 A1* | 12/2013 | Thompson | A01J 5/007 119/14.02 |
| 2014/0155785 A1* | 6/2014 | Haas | A61B 5/1038 600/595 |
| 2015/0107518 A1* | 4/2015 | Anglart | A01J 5/007 119/14.02 |
| 2016/0073614 A1* | 3/2016 | Lampe | A01L 11/00 600/408 |

OTHER PUBLICATIONS

International-Type Search Report, dated Apr. 18, 2012, from corresponding PCT application.

A. Pluk et al., "Automatic measurement of touch and release angles of the fetlock joint for lameness detection in dairy cattle using vision techniques", J. Dairy Sci., 2012, pp. 1738-1748, vol. 95, No. 4.

Ahmad Poursaberi et al., Online Lameness Detection in Dairy Cattle Using Body Movement Pattern (BMP), IEEE, 11th International Conference on Intelligent System Design and Applications, 2011, pp. 732-736.

Xiangyu Song et al., "Automatic detection of lameness in dairy cattle—Vision-based trackway analysis in cow's locomotion", Computers and Electronics in Agriculture, 2008, pp. 39-44, vol. 64, No. 1.

* cited by examiner

METHOD AND APPARATUS FOR DETECTING LAMENESS IN LIVESTOCK

TECHNICAL FIELD

The present invention concerns the detection of lameness in livestock. In particular, it relates to the non-invasive detection of lameness in cattle, but also to other four-legged animals, such as horses, sheep and goats.

BACKGROUND

All livestock is subject to lameness but dairy animals and specifically dairy cows are particularly vulnerable, due in part to the weight they carry, but also to their accommodation. In many modern diary farms cows are confined all year round in confinement systems with concrete floors. Over time, this surface can damage the hoof leading to lameness. Even in dairy farms that are pasture based, the animals have to stand on concrete floors in the milking parlour at least twice a day. In addition, the floor of the milking parlour is often wet, which can encourage infection.

Lameness can lead to a reduction in feed intake, a reduction in milk production and weight loss. Thus lameness has a drastic effect on the performance of a dairy animal. Lameness is conventionally detected by a herdsman by observing the movement of the animal and will often only be picked up once it has become severe requiring immediate and often costly treatment. Once an animal becomes lame, it can take several months to recover. Lameness thus represents a significant cost for livestock breeders and farmers in terms of time, financial expenditure for veterinary services, medication and treatment, and also for loss in production.

It is thought that the early detection of lameness can mitigate these losses as early treatment may enable an animal to recover more rapidly. A number of automatic lameness detection systems are known, however, these require the animal to perform some kind of movement, sometimes under controlled conditions, which, in a farm environment is often not practical or cost effective. U.S. Pat. No. 6,699,207 proposes a diagnostic system for detecting lameness in dairy cattle which consists of a system of plates placed over load cells provided at floor level and over which the animals must walk. The system determines and analyses the animal's limb reaction forces, weight, bilateral symmetry of limb reaction forces and other factors as the animal passes over the plates and compares these with reference data obtained when a healthy animal passes over the plate. The drawback of this system is that reference data must be provided, preferably for each animal, requiring all animals to walk over the system when healthy at least once. The system of plates is also cumbersome and large requiring adequate floor space and considerable installation costs.

Further systems propose the attachment of sensors to the animal to detect abnormal movement. A problem with these systems is how to ensure that the sensors remain fixed on the animal in what may be an inherently dirty environment without reverting to invasive techniques that require costly veterinary or specialist intervention and may cause unnecessary distress to the animal. WO 2006/009959 describes a system for monitoring the condition and wellbeing of dairy animals that includes a monitor unit fixed to a collar, strap, transdermal patch or ingested bolus carried by the cow that includes a number of sensors, one of which is an accelerometer. Lameness is determined by analysing the signals from the accelerometer to detect an abnormal gait, which could indicate lameness. A fixed unit is provided which collects data from the monitoring unit wirelessly and analyses this. A problem with this system is the complexity of the signals that will be produced as any movement of the cow, including raising or lowering its head, will be registered by the accelerometer. Added to this is the difficulty in ensuring that the accelerometer does not move on the cow. Moreover, determining signals that indicate an abnormal gait and possible lameness is complex and prone to error, resulting in unreliable results. WO 2006/009959 proposes a similar system for monitoring the gait of a horse wherein patches consisting of piezoelectric film are attached to each hoof of the horse. The signals produced are analysed and compared to reference signals, which are collected from the same animal or a group of other animals previously. This system must be used in a controlled and clean environment as the location of the sensors on the hooves of the animal would otherwise put them at risk of damage.

There is thus a need to improve on the automatic early detection of lameness.

SUMMARY

It is an object of the present invention to overcome the disadvantages of prior art arrangement and provide a device and method for detecting lameness in animals at an early stage that is simple to install, does not impact on the animal's normal routine and provides a rapid result.

This and further objects of the invention are provided in a device for detecting lameness in a standing animal comprising at least one optical imaging device, and a processing arrangement coupled with the optical imaging device. The optical imaging device is arranged in a position to capture at least one image showing the lower portions of at least one leg of an animal and to forward a captured image to the processing arrangement, wherein the processing arrangement is configured to analyse the image of said at least one leg to determine a condition of lameness when said at least one leg is held in a raised position on or above a floor surface.

It has been observed that when an animal is or is becoming lame, it tends to slightly lift the leg in question so as not to put weight on it when standing. By detecting whether a leg is held in a position, that differs from the normal flat standing position, whether in contact with a floor surface or held above this surface, the device is able to provide an early indicator of a possible problem to the farmer or stockman enabling further investigation and treatment. In this context, a raised position is intended to mean a position in which the animal's leg or foot will not bear the weight of the animal and thus defines a position in which the lower surface of the foot is not in contact with the floor over the whole of its surface. Furthermore, a floor surface may be a substantially flat surface designed to support the animal, or be composed of different levels with raised profiles or dips which encourage an animal to stand with her legs in a particular position to facilitate an operation such as cleaning, inspection or milking. In this case any part of the floor surface may be viewed as a reference surface for determining whether a leg is raised or not.

Preferably, the optical imaging device is adapted to capture a plurality of images at intervals over a predetermined period of time to ensure that the animal's leg is indeed held in a raised position and that an image has not been captured while the animal shifts its position.

In accordance with a preferred embodiment of the invention, the device includes an identification unit that is coupled to the processing arrangement and is arranged to communicate with a transponder carried by the animal and to extract from the transponder an identification code associated with the animal. By automatically identifying the animal through its code it is possible, firstly, to detect lameness in an individual subject without the presence of a herdsman and, secondly, to store this information individually for each animal as part of a larger health and/or production record. This data can then be used to monitor the progression of an ongoing condition, or to provide statistics for individual animals or a herd of animals.

Preferably, the optical imaging device comprises a camera. This may be a time of flight camera, which provides a depth measurement and thus a 3D image. Alternatively, the camera may be one that generates a 2D image, such as a CCD camera. Advantageously, the device comprises at least two cameras, enabling a 3D image to be generated using lower cost 2D cameras and additionally or alternatively to enable all legs of an animal to be viewed without obstruction.

In a particularly advantageous and cost-effective embodiment of the present invention, the camera is arranged to be used as part of an automatic or semi-automatic milking arrangement for enabling the determination of the position of the teats of a dairy animal. Such cameras are commonly used to determine the teat positions to enable teat cleaning, teat cup attachment and/or aftercare treatment. Combining a lameness detection function in the milking arrangement is a relatively simple modification and permits the detection to take place while the animal is confined and stationary as part of her normal routine.

The optical imaging device may conveniently be arranged in an animal stall having at least a floor surface, and be located in a position wherein the device is able to capture an image of at least one leg on or near the floor surface. This likewise ensures that the device can operate while the animal is at least partially confined, stationary and at close proximity to the device. Integrating the device in a feeding stall or a milking stall further ensures that the animal is occupied and substantially stationary for sufficient time to enable the device to operate.

The invention further resides in a milking stall comprising a lameness detection device, an automatic milking arrangement including a device for detecting lameness and a method for monitoring the condition of an animal in accordance with the appended claims.

BRIEF DESCRIPTION OF THE DRAWINGS

Further objects and advantages of the present invention will become apparent from the following description of the preferred embodiments that are given by way of example with reference to the accompanying drawings. In the figures.

DETAILED DESCRIPTION

Figure 1:
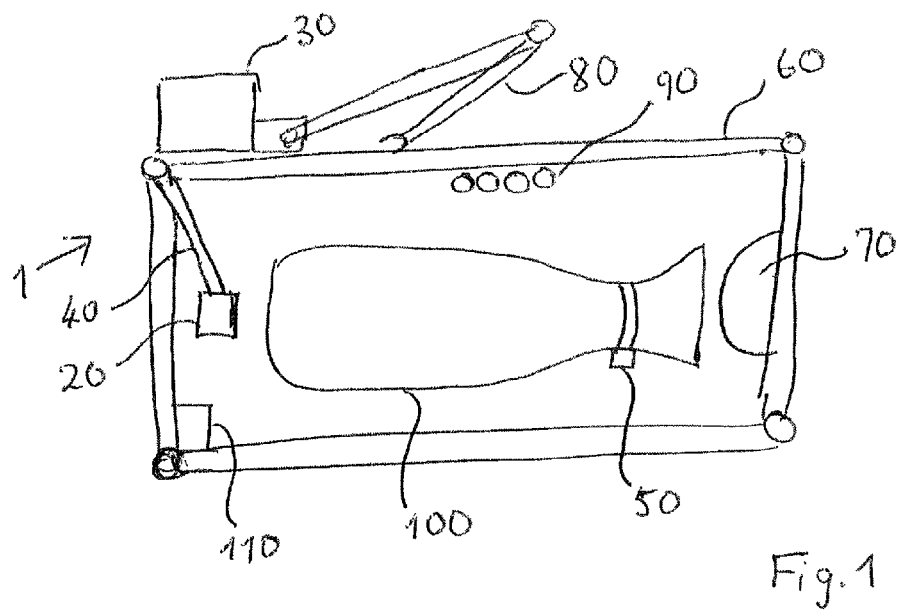
FIG. 1 schematically illustrates a lameness detection device in accordance with one embodiment of the present invention, FIG. 2 schematically illustrates an alternative view of the lameness detection device of FIG. 1.

Referring to FIG. 1 there is shown a stall, which in the exemplary embodiment is a milking stall 60 for milking dairy cows, in which is arranged a device for detecting lameness 1 in accordance with the present invention. As shown in FIG. 1, the stall 60 is made up of wall sections, which are essentially bars or barriers, one side of which may open to allow the entrance and exit of the animal. The outline of a cow 100 is also depicted in the stall 60. The stall 60 is further provided with a floor, which is not illustrated in detail. The floor is a hard, essentially planar surface and is preferably kept free of any soft material, such as straw, sawdust, sand or the like that may impede a clear view of an animals legs. However, the floor may include sections of different height and/or slope designed to prevent an animal placing her legs in certain areas and so to encourage a position that facilitates treatment, At the rear of the stall there is arranged a device for detecting lameness 1, which includes a processor 30 and an optical imaging element 20 that is coupled to the processor 30. The connection between the optical imaging element 20 and processor 30 may be achieved via a wire link. Alternatively, the connection may be wireless, for example, using infrared radiation or a wireless radio protocol, such as Bluetooth. The processor 30 includes data processing circuitry, such as a microprocessor or mini computer together with programme and data memory. The optical imaging element 20 is a camera, preferably a time of flight (TOF) camera, which permits a 3 dimensional image to be generated using a single image by emitting light pulses and for each pixel determining the time for light to be reflected back from an object. Cameras of this kind are well-known in the art and will not be described in more detail here. An example of a suitable camera is the SR4000 offered for sale by MESA Imaging AG. Further cameras are available from LMI Technologies Inc. and Fotonic Alternatively, the optical imaging element could be a CCD camera, or an arrangement of two or more TOF or CCD cameras. In the illustrated embodiment, the optical imaging element 20 is mounted on an arm 40 that may be movable and controllable by the processor 30 to change the position of the element 20. In particular, the arm may be articulated and/or telescopic allowing the displacement of the optical imaging unit 20 in the stall 60. In alternative embodiments the arm 40 may be fixed or the optical imaging element 20 fixedly mounted on part of the stall or on a separate arrangement on or near the floor.

An identification unit 110 is also disposed in the stall 60 and is coupled to the processor 30. Each animal is furthermore provided with a transponder 50 that stores a code identifying the animal. The transponder 50 may be carried on a collar around the animal's neck as shown in the figure, or be affixed to any other convenient attachment arrangement, such as an ear tag, head collar or leg strap. When an animal approaches the identification unit 110, the unit interrogates the transponder 50 to obtain the animal's identification code.

In the illustrated embodiment, the processor 30 is part of an automatic robotic milking system that includes a robot arm with gripper 80 that is able to pick up teat cups 90, either individually or collectively, carry these to the teats of a cow and attach each one to a teat. The robot arm 80 may also convey other equipment towards the teats, such as a cleaning device or a device for effecting a post-milking or after-care treatment. The various components and function of such a system are generally known in the art and will not be described in detail here. When the processor 30 receives an identification code of an animal from the identification unit 110 it may use this code to call up data stored for the cow in question, which may include the expected milk yield, the dimensions of the animal, the last known position of the teats and/or general health information. Advantageously, the optical imaging element 20 may also form part of the automatic robotic milking system and be used to determine the position of the udder and teats of an animal in order to allow the udder and/or teats to be cleaned by automatic cleaning means, to attach teat cups to each teat for milking and/or to automatically perform an after-treatment on the teats, such as a spray disinfectant, or the like. At the front end of the stall there is arranged a manger 70, into which a suitable feed such as concentrate is dispensed, preferably by means of an automatic feed dispensing arrangement that may also be coupled to the processor 30.

Figure 2:
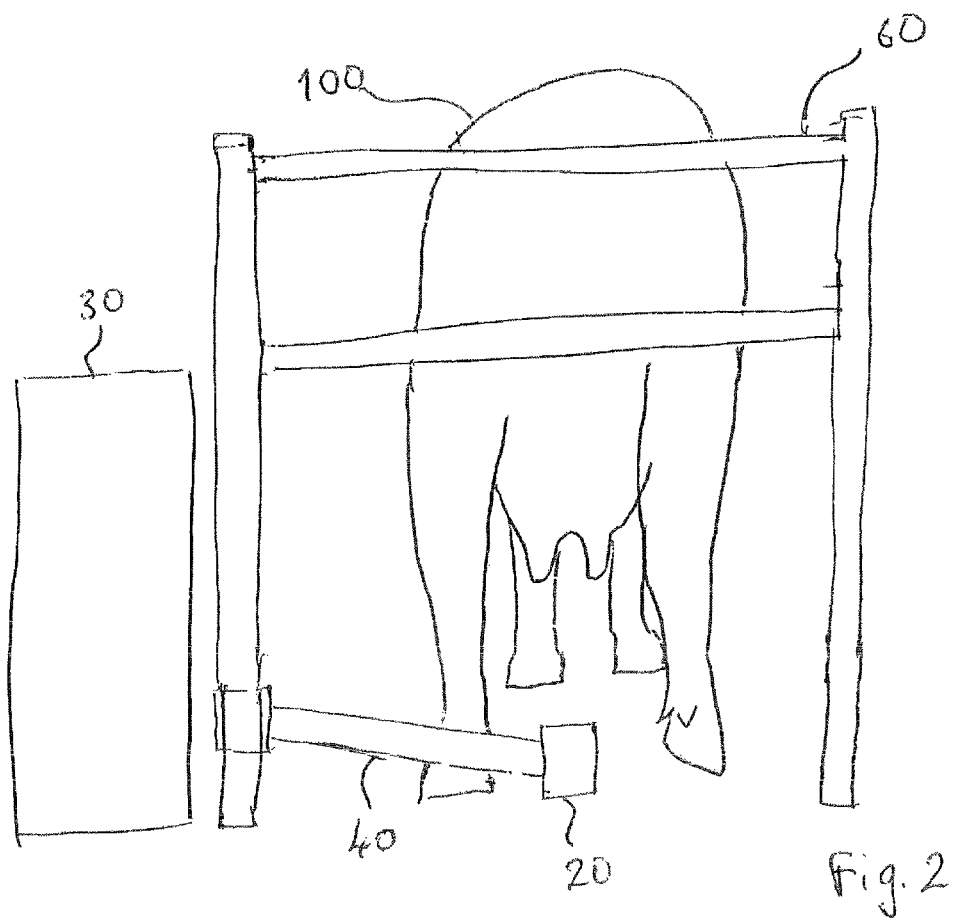

Turning now to FIG. 2 there is shown a rear side view of the milking stall 60 with the processor 30 shown to the left of the figure and the optical imaging unit 20 mounted on an arm 40, also mounted on a beam of the milking stall 60 to the left of the stall. As can be seen in FIG. 2, the optical imaging unit 20 is located at a position above the floor behind the animal 100 where it can capture an image of the lower part of at least one leg of the animal 100, but preferably of more than one leg. Depending on the stance of the animal 100 and the position of other equipment within the stall, it may be possible for the optical imaging unit 20 to capture an image that shows the lower part of all four legs of the animal 100.

The operation of the arrangement is as follows. When an animal 100 enters the milking stall 60 it is identified by the identification unit 110 which obtains the identification code from the transponder 50 attached to the animal 100. The animal 100 will then be milked according to the normal procedure, possibly preceded with cleaning and preparation and/or succeeded by an after treatment. The lameness detection device may be activated prior, during or after this milking operation. This is achieved by activating the optical imaging unit 20 to produce one or more images of the space within the stall 60. For the purpose of detecting lameness, the image captured must include at least one lower leg of the animal 100 and preferably all legs. When the optical imaging unit 20 is also used to determine the position of the teats of the animal 100 it may be possible to use a single image for both purposes. The signals captured by the optical imaging unit 20 are relayed to the processor 30 where the image or images are processed using a suitable algorithm to determine the objects and their various positions in the field of view.

Figure 3:
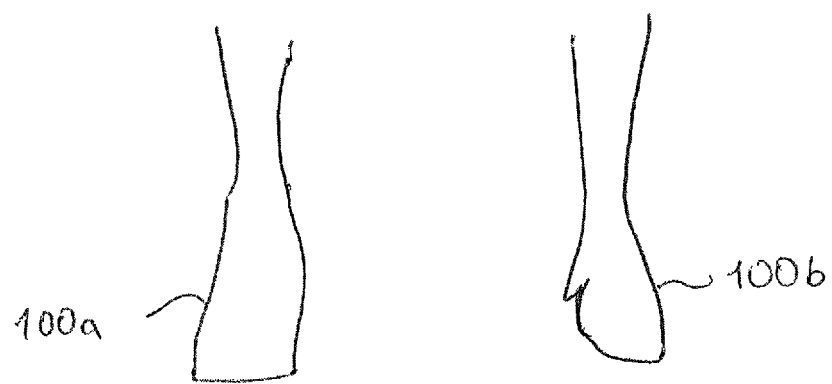
FIG. 3 shows the rear legs of an animal illustrating a possibly lame leg.

When processing the image to detect lameness, the algorithm is designed to first identify objects as the legs of the animal and secondly to recognise a hoof that is not placed flat on the ground. Reference is made in this regard to FIG. 3. FIG. 3 shows the lower part of the rear legs of the animal illustrated in FIG. 2. The left-hand hoof 100a is standing normally on the floor with the hoof flat and in contact with the floor. In contrast, the right-hand hoof 100b is not flat, but instead is raised slightly. The hoof may not be lifted completely from the floor to create a space between the hoof and the floor. However, the act of raising the leg slightly alters the silhouette of the hoof and also the three-dimensional shape of the hoof, so that it is possible to identify the anomaly based on the hoof shape. The same is true when an animal is lame in a front leg. The change in the silhouette means that it is possible to identify the raised leg even when a single 2D camera, e.g. a CCD camera, is used rather than a TOF camera that can provide a 3D image. Since it is possible that an animal may shift position in the stall from time to time, the optical imaging unit 20 is arranged to capture a number of images spaced at intervals and to compare the images to determine whether one or more hooves are held in an abnormal position during a predetermined period of time. For example, a hoof detected in a raised position in five successive images captured at intervals of around 2 s over a period of around 8 s would establish whether one or more of the animal's hooves are raised while the animal is stationary. Clearly this is only an example, and a series of fewer or of more images may be used, while the intervals between successive images may also be adjusted.

While in the illustrated embodiment, the optical imaging unit 20 is located at the rear of a stall and effectively views the front legs of the animal through the animal's rear legs, it is likewise possible to place the optical imaging unit 20 at a different position, e.g. at the side or even the front of the stall. When placed at the side of the stall, the camera could be arranged to pivot to enable two images to be taken, one of the front legs and the other of the rear legs. Alternatively, or in addition, two ore more cameras could be located around the stall 60 to ensure a clear view of all legs. This can also be used to generate a 3D image when 2D cameras, such as CCD cameras are used.

Once a possible lame leg has been detected using the device 1, this information can be stored together with the animal's identification code. An alert message may be produced, either on a display, or in the form of a printout. Alternatively, an alert message may be transmitted to a remote terminal, such as a remote pc, mobile phone or other portable communication devices to make the stockman aware of the animal's condition.

The advantage of locating the lameness detection device 1 in a milking stall is that the animal will remain standing for a certain period of time and it is possible to determine whether the animal is holding one or more of its legs away from the floor. Naturally, this is true regardless of the manner in which the animal is being milked, whether milking is fully automatic, semi-automatic with some procedures being carried out manually or manual. The device 1 can also be integrated in any form of parlour, i.e. a single or tandem milk box, a parlour with multiple milking stalls or a rotary platform parlour. The lameness detection device 1 can advantageously be integrated in a milking system and the periphery devices surrounding this system, so that the identification and alert functions of this system can be used for the detection of lameness. However, it is equally possible to provide the lameness detection device 1 as a stand-alone device. Locating the lameness detection device at a milking stall also enables detection to be performed regularly, possibly more than twice a day, so that an abnormal condition can be detected at the earliest possible stage. The lameness detection device 1 may also be arranged at other locations where animals are likely to stand for a period for time and, ideally, where they can be identified automatically. This includes feeding stalls, but also selection or sorting stalls, which could permit animals with suspected lameness to be diverted into a separation area, where they can subsequently be examined and, if necessary, treated. Such a selection or sorting stall could be placed in between areas that are subject to high traffic, for example between feeding and resting areas or a milking parlour and pasture so that the animals are routinely checked for lameness or the onset of lameness. The animal could be provided with fodder or concentrate in such a selection stall to encourage the animal to remain calm and stationary during lameness detection. The lameness detection device 1 could even be located at another area where animals naturally congregate without being confined in a stall, for example at a feeding table.

The invention claimed is:

1. A method of detecting lameness in a standing, stationary animal, the method comprising the steps of:
automatically capturing, using an optical imaging device, an image of a lower portion of a leg of the animal while the animal is standing and stationary, the lower portion of the leg in the image including a hoof of the leg, the hoof having a lower surface defining a first contact surface with a floor surface when the animal is standing and stationary on the floor surface;
receiving the image at a processor arrangement in communication with said optical imaging device; and
analyzing, at the processor arrangement, the image and generating, based on said analyzing, a determination indicating whether the lower leg captured by the image is in one of i) a flat position wherein the hoof is flat in contact with the floor, or ii) in a raised position wherein the hoof is either not flat against the floor surface or is distanced above the floor surface,
the processor arrangement outputting a determination of lameness in the animal when the determination indicates that the lower portion of a leg of the animal in the image is in the raised position.

2. The method of claim 1, wherein,
the optical imaging device automatically captures a plurality of images of the lower portion of the leg of the animal at different points in time over a predetermined period of time, and
the processor arrangement determines whether, in each of said images, the lower leg is in the flat position or in the raised position, and thereby generate plural individual image determinations, and
the generating of the determination of lameness in the animal includes the processor arrangement further evaluating the plural individual image determinations, the determination of lameness in the animal being generated when the leg is evaluated to be in the raised position throughout the predetermined period of time.

3. The method of claim 1, wherein,
the animal is confined within a stall comprised of wall sections when the optical imaging device is capturing the image of the lower portion of the leg of the animal, and
the optical imaging device comprises a camera that produces one of the group consisting of i) a two-dimension image, and ii) a three-dimension image from a single image of the camera.

4. The method of claim 3, wherein,
the camera is mounted relative to the stall in one of the group consisting of i) a fixed position, and ii) a mobile position, the mobile position allowing articulation of the camera or telescoping of the camera,
the camera produces a two-dimension image, and
the processor arrangement determines that the image indicates that the lower leg is in the raised position based on identifying an anomaly of a silhouette shape of the hoof in the image.

5. The method of claim 3, wherein,
the camera is mounted relative to the stall in one of the group consisting of i) a fixed position, and ii) a mobile position, the mobile position allowing articulation of the camera or telescoping of the camera,
the camera produces a three-dimension image, and
the processor arrangement determines that the image indicates that the lower leg is in the raised position based on identifying an anomaly of a three-dimensional shape of the hoof in the three-dimension image.

6. The method of claim 3, wherein,
said stall is a milking stall, and
said capturing step is performed while the animal is being milked, and
comprising the further step of using said camera as part of an automatic or semi-automatic milking arrangement to determine a position of teats of the animal.

7. The method of claim 3, wherein,
said stall is a milking stall, and
said capturing step is performed prior to the animal being milked.

8. The method of claim 3, wherein,
said stall is a milking stall, and
said optical imaging device captures the image after the animal is milked.

9. The method of claim 3, wherein,
said stall is a feeding stall, and
said capturing step is performed while the animal is at a feed station of said feeding stall.

10. The method of claim 1, wherein,
said capturing step utilizes two cameras located at different positions relative to the animal that capture a plurality of images of the lower portion of the leg of the animal, and
the processor arrangement uses the plural images from said two cameras.

11. A method of claim 1, comprising the further steps of:
automatically obtaining an identification code of the animal; and
storing data concerning the determined lameness of the animal output by the processor arrangement along with said identification code.

12. A system that detects lameness in a standing, stationary animal, the system comprising:
an optical imaging device that automatically captures an image of a lower portion of a leg of the animal while the animal is standing and stationary, the lower portion of the leg in the image including a hoof of the leg, the hoof having a lower surface defining a first contact surface with a floor surface when the animal is standing and stationary on the floor surface;
a processor arrangement in communication with said optical imaging device and that receives the captured image transmitted by the optical imaging device,
the processor arrangement configured to analyze the image and generate, based on said analyzing of the image, a determination indicating whether the lower leg is in either of i) a flat position wherein the hoof is flat in contact with the floor, or ii) in a raised position wherein the hoof is either not flat against the floor surface or distanced above the floor surface, and outputs a determination of lameness in the animal when the determination indicates that the lower portion of a leg of the animal in the image is in the raised position.

13. The system of claim 12, wherein, in operation,
said optical imaging device captures a plurality of images at different points in time over a predetermined period of time, and
said processor arrangement determines whether, in each said images, the lower leg is in one of the flat position or the raised position, and thereby generates plural individual image determinations, and the outputting of the determination of lameness in the animal includes the processor arrangement evaluating the plural individual image determinations, the determination of lameness in the animal being output when the leg is evaluated to be in the raised position throughout the predetermined period of time.

14. The system of claim 12, further comprising:
a stall comprised of wall sections configured to confine the animal while the optical imaging device captures the image,
wherein the optical imaging device comprises a camera that produces one of the group consisting of i) a two-dimension image and ii) a three-dimension image from a single image of the camera.

15. The system of claim 14, wherein,
the camera is mounted relative to the stall in one of the group consisting of i) a fixed position, and ii) a mobile position, the mobile position allowing articulation of the camera or telescoping of the camera,
the camera produces a two-dimension image, and
the processor arrangement determines that the image indicates that the lower leg is in the raised position based on identifying an anomaly of a silhouette shape of the hoof in the image.

16. The system of claim 14, wherein,
the camera is mounted relative to the stall in one of the group consisting of i) a fixed position, and ii) a mobile position, the mobile position allowing articulation of the camera or telescoping of the camera,
the camera produces a three-dimension image, and
the processor arrangement determines that the image indicates that the lower leg is in the raised position based on identifying an anomaly of a three-dimensional shape of the hoof in the three-dimension image.

17. The system of claim 14, wherein,
said stall is a milking stall, and
said camera captures the image while the animal is being milked, and
further comprising an automatic or semi-automatic milking arrangement, the camera operatively connected to the milking arrangement and the milking arrangement configured to use the camera to determine a position of teats of the animal.

18. The system of claim 12, wherein,
the optical imaging device comprises two cameras located at different positions relative to the animal, and the two cameras capture a plurality of images of the lower portion of the leg of the animal, and
said processor arrangement uses the plurality of images from said two cameras in making the determination whether the lower leg is in the flat position or the raised position.

19. A system of claim 12, further comprising:
an animal identification unit carried by the animal, including a transponder in communication with said processor arrangement,
said processor arrangement configured to extract from said transponder an identification code associated with the animal,
wherein said processor arrangement automatically obtains the identification code associated with the animal and stores data concerning the detected lameness of the animal with said identification code.

* * * * *